United States Patent
Itokawa

Patent Number: 4,725,578
Date of Patent: Feb. 16, 1988

[54] COMPOUNDS HAVING THERAPEUTIC EFFECT AND THE PREPARATION THEREOF

[75] Inventor: Hideji Itokawa, Tokyo, Japan

[73] Assignee: Tobishi Pharmaceutical Co., Ltd., Tokyo, Japan

[21] Appl. No.: 904,193

[22] Filed: Sep. 5, 1986

Related U.S. Application Data

[63] Continuation of Ser. No. 661,668, Oct. 16, 1984, abandoned.

[51] Int. Cl.$^4$ .............................................. A61K 37/02
[52] U.S. Cl. .................................................... 514/11
[58] Field of Search ........................... 536/17.4; 514/11

[56] References Cited

U.S. PATENT DOCUMENTS 4,476,299  10/1984  Itokawa ............................. 536/17.4

OTHER PUBLICATIONS

Chem. Pharm. Bull. 31 (4) 1424–1427(1983).
Chem. Abstr. vol. 102, (1985) 191224.

*Primary Examiner*—Delbert R. Phillips
*Attorney, Agent, or Firm*—Bucknam and Archer

[57] ABSTRACT

New compounds of the following general formula:

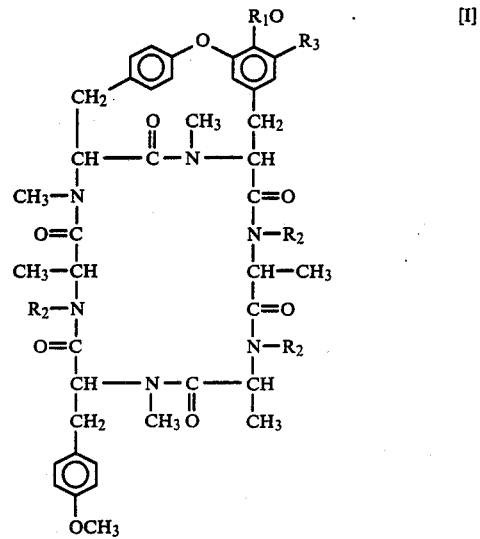

wherein $R_1$ is acyl, alkyl, cycloalkyl, carboxyalkyl or ester thereof, heterocyclic group, saccharide residue or hydrogen atom, $R_2$ stands for hydrogen atom or a lower alkyl and $R_3$ represents hydrogen atom or a nitrogen-containing group, are provided, among these, some of the compounds to be isolated and purified from a plant belonging to Genus Rubia, other compounds being prepared by chemically modifying the isolated compounds with various kind of substituents and these new compounds having therapeutic effect, in particular such as antineoplastic, emetic, anorexigenic, psychotropic, vasoconstrictive, papaverinic, antiperkinsonian and/or antidiuretic effect.

4 Claims, 3 Drawing Figures

COMPOUNDS HAVING THERAPEUTIC EFFECT AND THE PREPARATION THEREOF

This is a continuation of application Ser. No. 661,668, filed Oct. 16, 1984, now abandoned.

BACKGROUND OF THE INVENTION

The present invention relates to new compounds having therapeutic effect and a method for preparing thereof. Some of the new compounds are ingredients of the plant belonging to Genus Rubia and others are derivatives of the ingredient.

Up to now, there have been many attempts to obtain antineoplastic extracts from plants. Among such extracts, such as alkaloid-containing material extracted from a plant of colchicum autumnal (*J. Chem. Soc.*, 1940, 194) or vinca rosea (*J. Am. Chem. Soc.*, 1964, 86, 1440); one kind of lignan from podophyllum peltatum (*J. Am. Chem. Soc.*, 1953, 75, 235); and anthamacrolidic material having a similar molecular structure to rifamycin, which is extracted from a plant of celastraceae are well known. In addition, among materials extracted from a lower plant, mushroom, protein-polysaccharide body extracted from coriolus versicolor is, for instance, well known and has already been on the market (GAN TO KAGAKURYOHO, 1974, 1, 251). Nevertheless, only a few of these extracts have practically been utilized as a medicine.

Furthermore, a number of workers have made great efforts to obtain a single product having an exellent pharmacological action from plants, however, only a few of the workers succeeded in such attempt.

On the other hand, a number of studies have been carried out in order to get these kind of medicine by a chemical synthesis, however, almost all studies was discontinued without any remarkable success. This was because such synthetic medicines exhibited serious side-effects.

SUMMARY OF THE INVENTION

Under such circumstances, the inventor has paid attention to medicinal plants and, he has close and concentrated study to obtain useful ingredients from the medicinal plants. The medicinal plants have been used as a folk medicine for a long time, even at the present time due to their low toxicity and a moderate pharmacological action and even in the modern medical field, the effects attained by the medicinal plants have been reconsidered. Thus, it is found that the crude extract from madder (Rubia Spp) shows an excellent therapeutic effects and that a single product which has a strong antineoplastic action may be obtained by purifying the crude extract, and thus the inventor completed this invention.

The principal object of this invention is to provide new compounds having therapeutic effect.

Another object of this invention is to provided a process for preparing said new compounds.

Other objects of this invention and features thereof will be more apparent from the disclosure hereunder described.

New compounds according to the present invention are represented by the following general formula [I]:

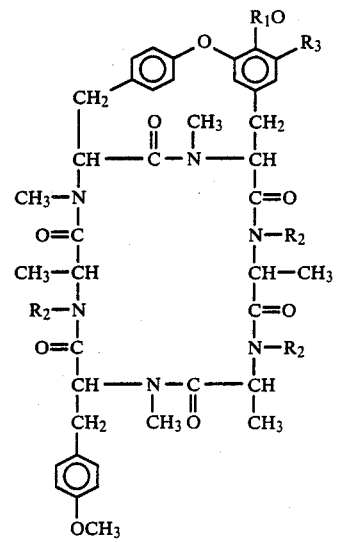

wherein $R_1$ represents an acyl group of —COA (A being a branched or linear, saturated or unsaturated $C_1$–$C_{20}$ alkyl group; phenyl or a phenyl substituted by a halogen atom, a lower alkyl, nitro or amino group; benzyl or styryl group unsubstituted or substituted by a halogen atom, a lower alkyl, nitro or amino group); a linear or branched $C_1$–$C_{20}$ alkyl group; a $C_3$–$C_6$ cycloalkyl group unsubstituted or substituted by lower alkyl, amino, nitro or a halogen atom; a $C_1$–$C_5$ carboxyalkyl group or an ester thereof with a $C_1$–$C_5$ alcohol; heterocyclic group; a saccharide residue; —$SO_2CH_3$ or hydrogen atom, $R_2$ represents hydrogen atom or a lower alkyl group and $R_3$ is hydrogen atom or a nitrogen-containing group such as amino, nitro.

It has been found that the compounds of the present invention have antineoplastic activity and have therapeutic effect, in particular such as emetic, anorexigenic, psychotropic, vasoconstrictive, papaverinic, antiperkinsonian and/or antidiuretic action.

DETAILED DESCRIPTION OF THE INVENTION

Figure 1:
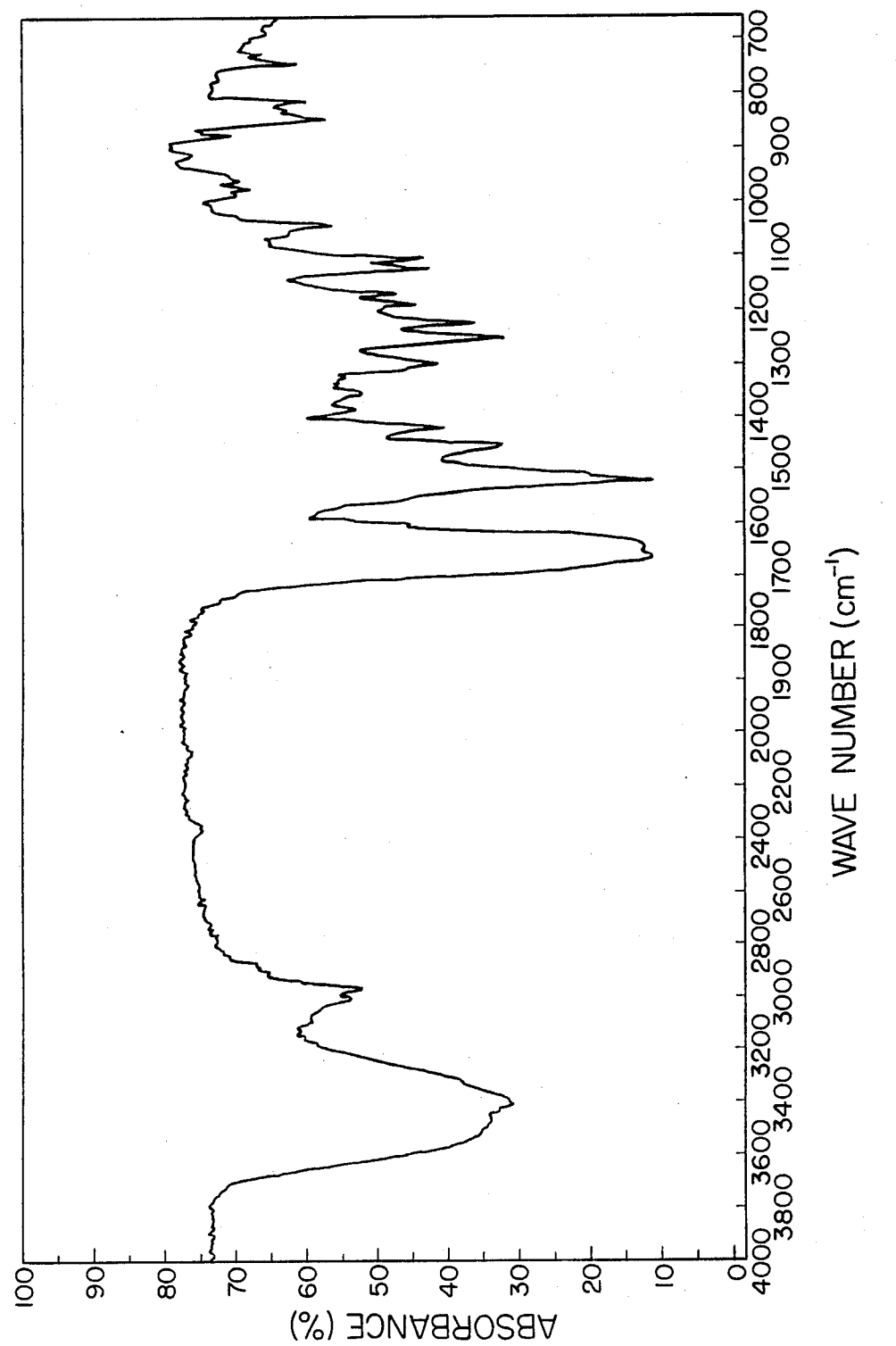
FIGS. 1 to 3 attached to the specification show the results of I.R. spectra observed for the compounds obtained in the Example 1 i.e., compound TPC-A and methylester derivative thereof and obtained in the Example 22, acetylated derivative of TPC-A respectively.

The *Rubia akane* used as a starting material from which the compounds TPC-A and the methylether derivative thereof are isolated is a perennial bine growing spontaneously in fields and mountains in the world. The yellow red root thereof has been used as blood cleaner, emmenagogue and hemostatics in the field of Chinese Orthodox Medicine and as a folk medicine for treating cold, cardiopathy and contusion in the form of decoction.

It is known that the Rubia Spp includes anthraquinones, nepetalactones, triterpenoids, saponins, alkaloids, however, no individual active component has ever been extracted or isolated.

The compound TPC-A having a hydroxyl group, which may be extracted and isolated from the *Rubia akane* and *R. cordiforia* has antineoplastic effect by itself and is assumed to have effect as other pharmacologically active ingredients. Furthermore, it is useful as an intermediate for preparing derivatives thereof which may be obtained by chemically modifying the free hydroxyl group and/or imino group thereof.

The compound TPC-A may be extracted from the root of *Rubia akane* and *R. cordiforia* by subjecting the dried root of *Rubia akane* and *R. cordiforia* to the extraction with a solvent such as methanol, ethanol, chloroform and ethyl acetate, concentrating the extract and subjecting the crude concentrated extract to the isolation and purification with the aid of the chromatography.

The methylether derivative of TPC-A may also be extracted from the root of *Rubia akane* and *R. cordiforia* as a different fraction from that of the TPC-A according to the same procedure. In addition, this compound may also be prepared by methylation of the compound TPC-A at the free hydroxyl group thereof in a suitable solvent. This compound may also be used as a starting material of other derivatives.

In the methylation reaction, an alcohol, an ether or an aqueous solvent may be used as a suitable solvent depending on the methylating agent used. Furthermore, a known methylating agent such as methyl halide, diazo methane or dimethyl sulfate may be used and the methylation of the compound TPC-A may be carried out according to a conventional methylation reaction.

During the extraction procedure, if the extraction is carried out by the column chromatography on active carbon, as an eluent it may be preferred to use less polar solvent than the extract, such as benzene, chloroform, ethyl acetate, methanol or the mixture thereof. While the separation is being carried out by the liquid chromatography, it is preferred to use reversed phase chromatographic column such as C-18 (manufactured by Waters Associates Inc.), RP-8 or RP-18 (sold by Merck & Co., Inc.) as well as a column of silicagel treated with ODS.

Other derivatives of TPC-A or methylether thereof may be prepared by the following procedures.

Among new compounds of the invention, the compounds in which $R_1$ is an alkyl, a cycloalkyl or a carboxyalkyl or ester thereof may easily be prepared by reacting the compound TPC-A isolated from the madder with an alkylating agent such as alkyl halide, methylating agent, cycloalkyl halides or carboxyalkyl halides or ester thereof. There may be mentioned as the alkylating agent $C_1$ to $C_{20}$ alkyl halides, for example bromides, $C_3$ to $C_6$ cycloalkyl harides, for example bromides, $C_1$ to $C_5$ carboxyalkyl harides such as bromides or lower alkyl ester thererof.

The alkylation of the OH group on a phenyl ring has been well known and in the present invention, the alkylation of the compound TPC-A is carried out according to a conventional method.

The compounds in which $R_1$ is an acyl group may be prepared by reacting the compound TPC-A with an acylating agent according to a conventional acylation method. As the acylating agent, acylhalides or acid anhydrides such as acetic anhydride, propionic anhydride, butyric or isobutyric anhydride, crotonic anhydride, valeric anhydride, caproic anhydride, enanthic anhydride, caprylic anhydride, capric anhydride, stearic anhydride, benzoic anhydride, O-,m-,p-chlorobenzoic anhydride, m-,p-nitrobenzoic anhydride, cinnamic anhydride, phenylacetic anhydride and chloride or bromide of these acids may be used in the present invention.

When a methane sulfonic acid halide is used instead of the acylating agent, methane sulfonic acid ester of TPC-A may be prepared in the same manner.

The compounds in which $R_3$ is a nitrogen-containing group may be prepared, for example by nitrating TPC-A and in case of need, reducing the nitro group according to a conventional nitration or reduction method.

The compounds in which at least one of $R_2$ are methyl group may be prepared by methylation of methylether derivative of TPC-A with a known methylating agent such as diazomethane, methyl halides, in particular iodide, dimethyl sulfate under the presence of an alkali hydroxide, an alkali carbonate or potassium fluoride.

The compounds in which $R_1$ is a sugar moiety residue may be prepared by the reaction between TPC-A and an activated and protected saccharide under the presence of a catalyst such as sodium hydride, silver oxide, silver perhydrochloride, silver salt. The activation of the saccharide may be carried out according to a conventional process and the protective group may be, for instance, acetyl, benzoyl, benzyl, and other acyl groups which may be removed under mild conditions.

Sugar moieties which is used in the present invention may be glucose, galactose, rhamnose, fructose, or xylose.

The present invention will be illustrated more concretely by the following non-limitative examples.

EXAMPLE 1

(i) Extraction

To 500 g of the dried starting material (root of *Rubia cordiforia*), 1 l of methanol was added and the extraction was continued in hot water bath for 3 hours with heating and then the extract was separated from the residue by filtration. The extraction was again carried out with respect to the residue by adding 1 l of fresh methanol. After repeating such extraction procedure, the resulting extracts were combined together and concentrated in vacuo to obtain 27 g of crude extract. Then 25 g of said crude extract was dissolved in 200 ml of methanol and the solution was introduced into a column filled with 250 g of active carbon for chromatography (manufactured and sold by Wako Inc.). After washing the column with methanol, the elution was carried out with chloroform-methanol and chloroform and the resulting eluted fractions were combined together and then concentrated in vacuo to obtain 10 g of oily material of reddish brown color.

In a small amount of chloroform, 9 g of the oily material was dissolved and was adsorbed onto a column filled with 400 g of silicagel. Then, the column was washed with chloroform, chloroform-ethyl acetate mixed solvent and ethyl acetate in this order, before the elution was carried out with chloroform-methanol mixture. The resulting elute was gathered and concentrated in vacuo to get 1.4 g of oily material.

Further, 1.3 g of the oily material was dissolved in a small amount of chloroform, then the solution was adsorbed onto a column filled with 150 g of silicagel and the column was washed with chloroform and chloroform-methanol mixture (100:1) followed by the elution with chloroform-methanol mixture (100:3). The fractions eluted were gathered and combined, then concentrated in vacuo and thus 250 mg of solid material was obtained.

The resultant solid was dissolved a small amount of chloroform-methanol mixture and after developing the solution on a TLC plate, Art 7544 (Merck & Co., Inc.) with the aid of chloform-methanol (100:15) mixed solvent, the resulting bands having dark blue color under irradiation of U.V. ray (254 nm), which correspond to $R_f$ of 0.60 to 0.71 and 0.50 to 0.59 respectively were packed into separate columns and each column was eluted with chloroform-methanol mixture, then after the evaporation to dryness in vacuo, 56 mg and 24 mg of light brown colored solid material were obtained from each fraction having low or high $R_f$ value respectively.

The solution of 40 mg of the solid material (low $R_f$) in 45% aqueous acetonitrile was subjected to preparative HPLC by using Micro Bondapack C-18 column (Waters Associates Inc.) and 45% aqueous acetonitrile solution as developing solvent, while the absorblance at 254 nm was used as an indication and the elute was evaporated to dryness in vacuo to get 24 mg of white powder (TPC-A). If desired, the procedure of preparative HPLC may be repeated to further purify the product.

The same procedure was repated as to the solution of 20 mg of the other solid material (high $R_f$) in 45% aqueous acetonitrile and 12 mg of white powder (methylether derivative of TPC-A) was obtained. The white powder was recrystallized from methanol and 10 mg of colorless needle crystal was obtained.

(ii) By using 100 g of dry *Rubia akane*, the above procedures (i) were repeated and 7.3 mg of TPC-A and 4.9 mg of the methylether derivative thereof were obtained.

(iii) Preparation of the methylether of the compound TPC-A

In a small amount of methanol, 10 mg of the compound TPC-A was dissolved and further 5 ml of diazomethane in ether was added. After leaving the solution to standing with cooling by ice water for 1 hour, the solution was evaporated to dryness in vacuo and the resulting white powder was recystallized from methanol to obtain 8 mg of colorless needle crystal.

The resultant material was identified to be the methylether derivative of TPC-A in the light of the data of N.M.R. and I.R. measurement.

The physical and chemical properties of these compounds, TPC-A and methylether thereof derived from the plant madder are shown in the following Table 1.

Figure 2:
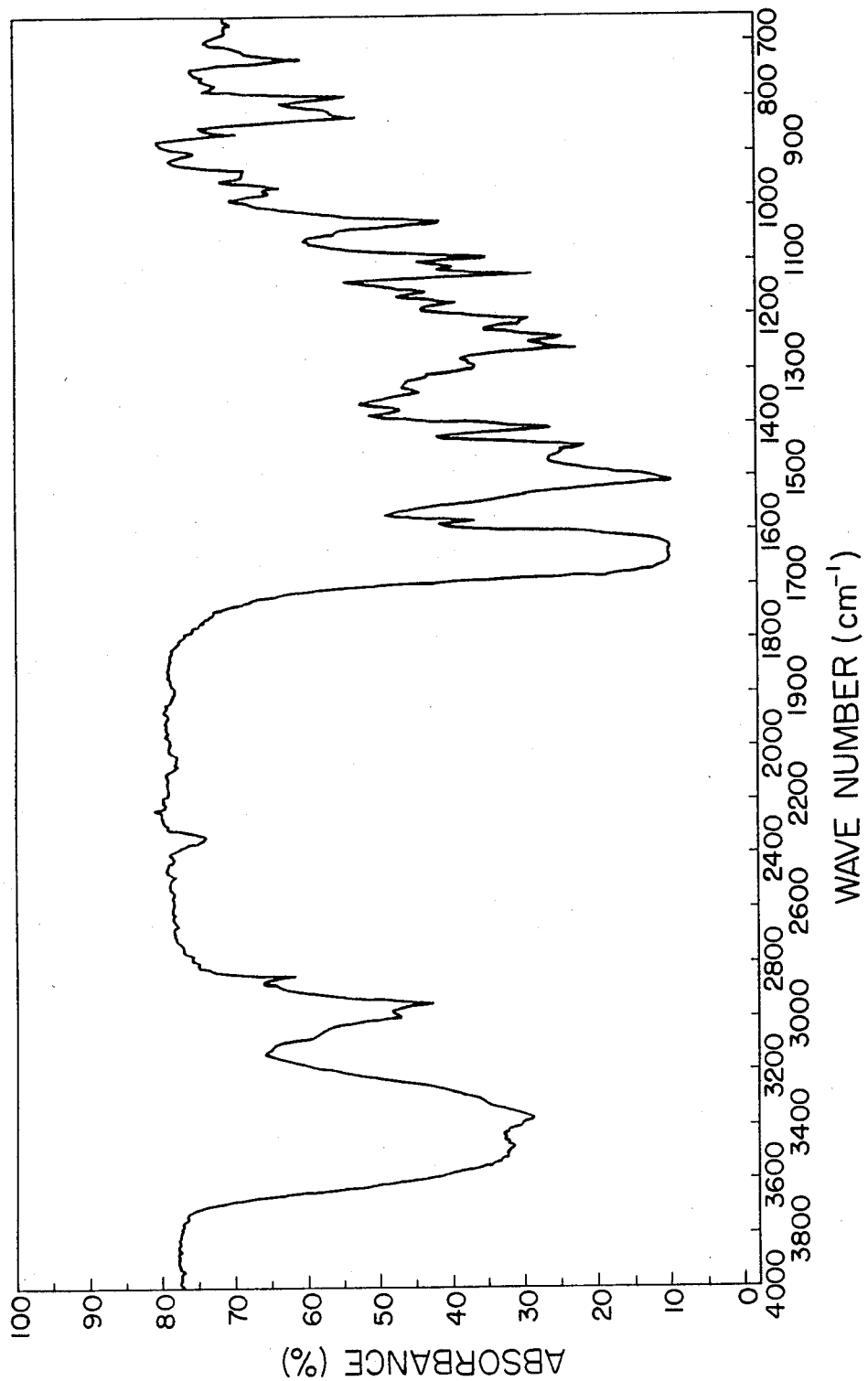
Figure 3:
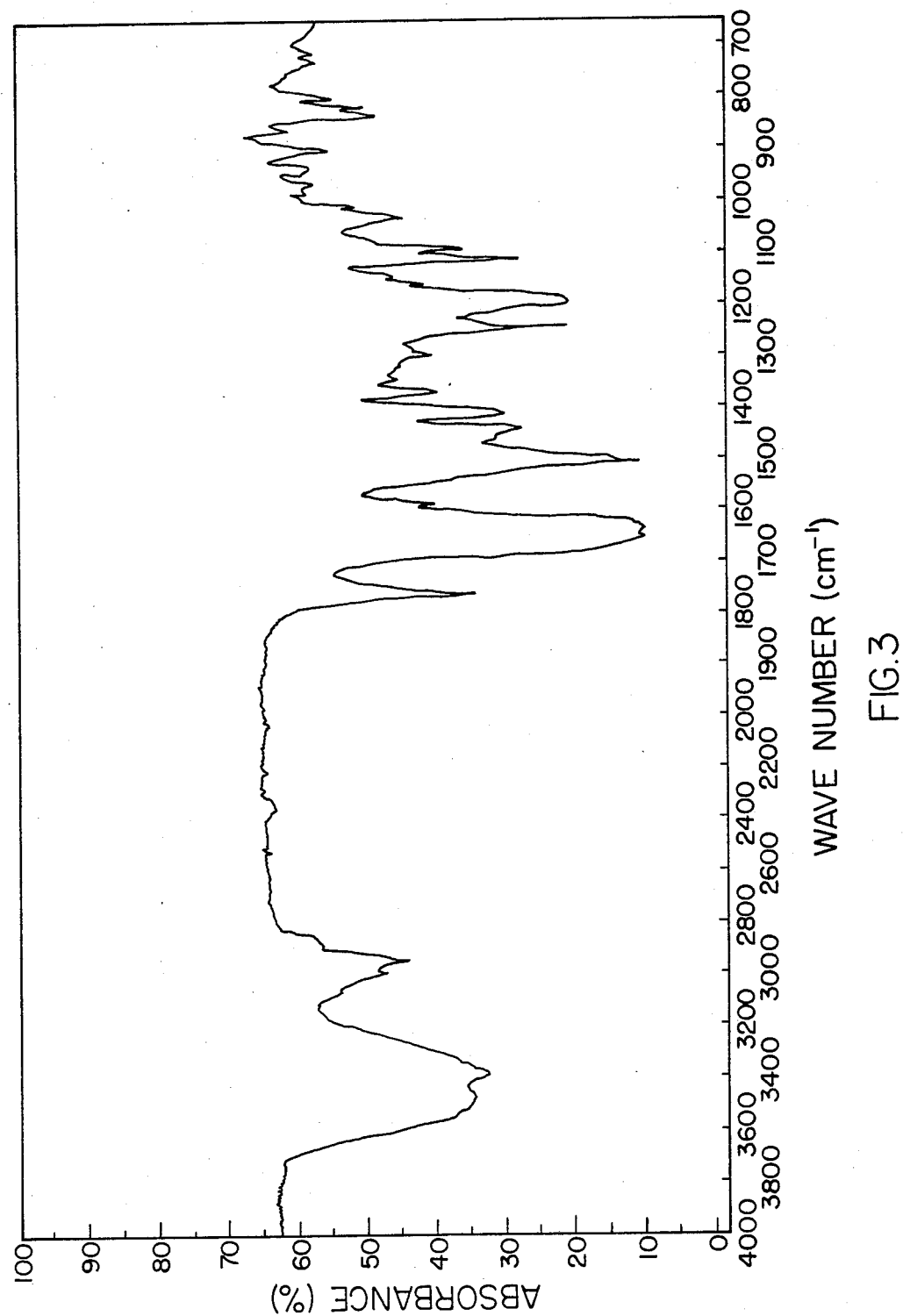

Furthermore, charts of I.R. spectra are given in FIGS. 1 and 2.

TABLE 1

| Properties | TPC-A | Methylether of TPC-A |
|---|---|---|
| Molecular weight* | 756 | 770 |
| Appearence | white powder | colorless needle |
| M.P. | about 235° C., gradually becoming brownish (no clear decomposition point) | >280° C. (no clear decomposition point) |
| specific rotatory power, $[\alpha]_D$ | −220° (CHCl₃, C = 0.1) | −224° (CHCl₃, C = 0.25) |
| U.V., $\lambda_{max}^{EtOH}$ | 276 nm; Θ = 3800  282 nm; Θ = 3300 | 276 nm; Θ = 3800  282 nm; Θ = 3300 |
| N.M.R., ($\delta_{ppm}$)** | 2.70(3H,s), 2.86(3H,s)  3.10(3H,s), 3.77(3H,s) | 2.70(3H,s), 2.86(3H,s)  3.12(3H,s), 3.78(3H,s)  3.92(3H,s) |
| I.R.*** | FIG. 1 | FIG. 2 |

*Molecular weight was determined by FD-MS.
**Proton NMR measurement was carried out by using CDCl₃ as solvent and Si(CH₃)₄ as internal standard, at 100 MHz.
***I.R. data was obtained according to KBr method.

EXAMPLES 2 TO 17

To a mixed solvent of tetrahydrofuran (4 ml), methanol (8 ml) and water (2 ml), 100 mg of TPC-A was added and further 20 mg of n-hexylbromide and excess amount of anhydrous potassium carbonate were added, then the mixture was subjected to reflux in a oil bath heated to 100° C. After completion of the reaction and discontinuing the heating, water was added to the reaction solution, the solution was extracted with ethylacetate and the extract was washed with saturated sodium chloride solution. Then, the washed extract was dried over anhydrous magnesium sulfate, the solvent was distilled off in vacuo, the residue obtained was washed with n-hexane and was purified by P-TLC. The product thus obtained was recrystallized from methanol and 63 mg of n-hexylether of the compound TPC-A was obtained as colorless crystal.

According to the same procedure, except that a n-alkyl bromide shown in Table 1 were used instead of n-hexyl bromide, the corresponding n-alkylether derivatives were obtained.

The physical properties of these products were also illustrated in Table 2.

TABLE 2

| Example | $R_1$ | m.p.(°C.) (decomp) | $[\alpha]_D$(CHCl₃) | T(°C.) |
|---|---|---|---|---|
| 2 | (CH₂)₅CH₃ | 261–268 | −178 | 26 |
| 3 | CH₂CH₃ | 219–225 | −194 | 25 |
| 4 | (CH₂)₂CH₃ | 212–217 | −193 | 25 |
| 5 | CH(CH₃)₂ | 213–220 | −194 | 26 |
| 6 | (CH₂)₃CH₃ | 210–216 | −192 | 25 |
| 7 | (CH₂)₄CH₃ | 214–221 | −191 | 25 |
| 8 | (CH₂)₆CH₃ | 245–250 | −189 | 26 |
| 9 | (CH₂)₇CH₃ | 243–249 | −178 | 27 |
| 10 | (CH₂)₈CH₃ | 245–248 | −169 | 26 |
| 11 | (CH₂)₉CH₃ | 242–247 | −198 | 26 |
| 12 | (CH₂)₁₀CH₃ | 228–235 | −179 | 26 |
| 13 | (CH₂)₁₁CH₃ | 240–242 | −189 | 26 |
| 14 | (CH₂)₁₂CH₃ | 238–242 | −186 | 26 |
| 15 | (CH₂)₁₇CH₃ | 228–235 | −153 | 26 |
| 16 | 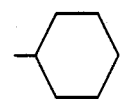 | 215–222 | −171 | 25 |

TABLE 2-continued

| Example | R₁ | m.p.(°C.) (decomp) | $[\alpha]_D$(CHCl₃) | T(°C.) |
|---|---|---|---|---|
| 17 | (cyclopropyl) | 229–233 | −155 | 26 |

EXAMPLE 18

(i) The procedures of the Example 2 were repeated except using methyl bromoacetate instead of n-hexyl bromide and thus the hydroxy-carbonylmethylether (1) of TPC-A was obtained as colorless crystal.

(ii) The product (1) obtained in (i) was treated with diazomethane and recrystallized from methanol to obtain methylester (2) of the product (1) as colorless crystal. The physical properties are shown in Table 3.

EXAMPLE 19

(i) By using ethyl bromobutyrate instead of methyl bromoacetate, the step (i) in Example 18 was repeated to prepare hydroxycarbonylpropylether (1) and ethoxycarbonylpropylether (2) of TPC-A.

(ii) The product (1) was treated with diazomethane and then recrystallized from methanol to obtain methoxycarbonylpropylether of TPC-A as colorless crystal. The physical properties of these compounds are shown in Table 3.

TABLE 3

| Example | R₁ | m.p.(°C.) (decomp) | $[\alpha]_D$(CHCl₃) | T(°C.) |
|---|---|---|---|---|
| 18(1) | CH₂COOH | 211–215 | −141 | 25 |
| 18(2) | CH₂COOCH₃ | 201–207 | −161 | 24 |
| 19(1) | (CH₂)₃COOH | 223–228 | −140 | 24 |
| 19(2) | (CH₂)₃COOCH₂CH₃ | 181–186 | −188 | 24 |
| 19(3) | (CH₂)₃COOCH₃ | 178–184 | −171 | 25 |

EXAMPLE 20

In 4 ml of a mixed solvent of anhydrous ethylacetate (19 ml) and 5% anhydrous hydrochloric acid containing ethylacetate (1 ml), 100 mg of the compound TPC-A was dissolved, further 0.4 ml of 2,3-dihydropyran was added and after sealing the reaction vessel the mixture was left to stand overnight at 5° C. After the completion of the reaction, ethylacetate was added and the solution was washed with saturated sodium chloride aqueous solution, then dried over anhydrous magnesium sulfate. The solvent was distilled off in vacuo and the residue was washed with n-hexane followed by the purification by P-TLC. The resultant crystal was recrystallized from methanol and 55 mg of tetrahydropyranylether of TPC-A was obtained as colorless crystal, mp. 286 to 289 (decomp), $[\alpha]_D^{26}$ −157° (CHCl₃).

EXAMPLE 21 TO 39

In 5 ml of anhydrous pyridine, 50 mg of TPC-A was dissolved and 15 ml of caproyl anhydride was added dropwisely under stirring. After leaving the solution standing overnight, at room temperature, anhydrous toluene was added to the reaction solution and then the solvent was distilled off in vacuo. The resulting residue was washed with n-hexane and the precipitates obtained was recrystallized from methanol to obtain 38 mg of caproate of TPC-A as colorless crystal.

The same procedures were repeated except using other acids (inclusive of acid anhydrides or methane sulfonyl chloride) corresponding to the residue listed in the following Table 4 instead of caproyl anhydride and the corresponding products shown in Table 4 were obtained as colorless crystal. the physical properties of these product are shown in Table 4.

TABLE 4

| Example | R₁ | m.p.(°C.) (decomp) | $[\alpha]_D$(CHCl₃) | T(°C.) |
|---|---|---|---|---|
| 21 | CO(CH₂)₄CH₃ | 205–210 | −178 | 19 |
| 22 | COCH₃ | 228–241 | −190 | 18 |
| 23 | COC₂H₅ | 222–228 | −171 | 21 |
| 24 | CO(CH₂)₂CH₃ | 196–201 | −165 | 21 |
| 25 | COCH(CH₃)₂ | 225–232 | −140 | 22 |
| 26 | COCH=CHCH₃ | 215–223 | −88 | 22 |
| 27 | CO(CH₂)₃CH₃ | 203–208 | −178 | 21 |
| 28 | CO(CH₂)₅CH₃ | 195–200 | −182 | 19 |
| 29 | CO(CH₂)₆CH₃ | 190–195 | −173 | 19 |
| 30 | CO(CH₂)₈CH₃ | 174–180 | −174 | 19 |
| 31 | CO(CH₂)₁₆CH₃ | 105–110 | −131 | 19 |
| 32 | CO—C₆H₅ | 240–245 | −188 | 22 |
| 33 | CO—(2-Cl-C₆H₄) | 219–224 | −171 | 23 |
| 34 | CO—(3-Cl-C₆H₄) | 221–226 | −160 | 23 |
| 35 | CO—(4-Cl-C₆H₄) | 225–231 | −155 | 23 |
| 36 | CO—(3-NO₂-C₆H₄) | 224–230 | −135 | 26 |
| 37 | CO—(4-NO₂-C₆H₄) | 197–202 | −140 | 26 |
| 38 | COCH=CH—C₆H₅ | 330–335 | −150 | 23 |
| 39 | SO₂CH₃ | 218–225 | −172 | 26 |

EXAMPLE 40 TO 45

Into an egg-plant type flask, 40 mg of thallium ethoxide was introduced and 2 mg of anhydrous ethanol was added, then the solution was stirred. Then, 110 mg of TPC-A and 1 ml of anhydrous tetrahydrofuran were added and stirred at room temperature for 3 hours and thereafter the solution was subjected to distillation to remove solvent, in vacuo, the resultant thallium salt of TPC-A was suspended in 2 ml of anhydrous tetrahydrofuran and a solution of 4-methyl Valeryl chloride (20 mg) in 1 ml of anhydrous tetrahydrofuran was added in a dropwise manner under stirring. Then the stirring was continued for two hours, the reaction solution was filtered to remove solid content, the filtrate was subjected to distillation in vacuo, and the resulting residue was washed with n-hexane followed by P-TLC purification. The product was subjected to recrystallization from methanol and 75 mg of 4-methyl valerate was obtained as colorless crystal.

The same procedures were repeated with using other acid chlorides which correspond to the residue listed in Table 5 instead of 4-methyl valeric acid and the corresponding products having a substituent listed in Table 5 were prepared.

Physical properties thereof are also shown in Table 5

TABLE 5

| Example | $R_1$ | m.p.(°C.) (decomp) | $[\alpha]_D$(CHCl$_3$) | T(°C.) |
|---|---|---|---|---|
| 40 | CO(CH$_2$)$_2$CH(CH$_3$)$_2$ | 285–292 | −181 | 19 |
| 41 | CO(CH$_2$)— | 205–212 | −179 | 19 |
| 42 | COCH$_2$CH(CH$_3$)CH$_2$CH$_3$ | 193–198 | −164 | 19 |
| 43 | COCH(CH$_3$)(CH$_2$)$_2$CH$_3$ | 195–201 | −178 | 19 |
| 44 | COCH=CH(CH$_2$)$_2$CH$_3$ | 268–274 | −164 | 20 |
| 45 | COCH$_2$CH=CHC$_2$H$_5$ | 198–203 | −183 | 20 |

EXAMPLE 46

(i) In 3 ml of acetic acid, 100 mg of TPC-A was dissolved and a solution of copper nitrate (40 mg) in 3 ml of acetic acid was added under stirring. When the color change of the reaction solution from blue to green took place under the continuation of stirring, water was added to cease the reaction and the product was extracted with ethyl acetate. After washing the extract with saturated sodium chloride solution and drying the extract over anhydrous magnesium sulfate, the extract was subjected to distillation to remove solvent, in vacuo and the product was recrystallized from methanol to obtain nitro compound of TPC-A at α-position of phenol thereof (108 mg) as yellow needle crystal having m.p. of 244°–250° C. (decomp) and $[\alpha]_D^{22}$ of −232° (CHCl$_3$).

(ii) The reaction product of the step (i) was treated with diazomethane and the product was recrystallized from methanol to form nitro compound of the methylether derivative of TPC-A as colorless crystal having m.p. of 225°–232° C. (decomp) and $[\alpha]_D^{23}$ of −187° (CHCl$_3$).

EXAMPLE 47

(i) To 7.5 ml of water, 90 mg of sodium borohydride was added and under stirring, small amount of 5% Pd/C was added, and then 130 mg of the product (Example 46(i)) in 15 ml of methanol was added dropwise. After completion of the reaction, water was added and the reaction product was extracted with ethylacetate. The extract was washed with saturated sodium chloride solution, then dried over anhydrous magnesium sulfate, and then the solvent was distilled off in vacuo followed by purification by P-TLC to form aminated compound of TPC-A at α-position of phenol thereof (64 mg) having m.p. of 238°–243° C. (decomp) and $[\alpha]_D^{25}$ of −199 (CHCl$_3$).

(ii) The product obtained in the Example 46(ii) was treated with the above procedures (i) and the resulting product was subjected to recrystallization with methanol to obtain the aminated compound of the methylether derivative of TPC-A having m.p. of 225° to 231° C. (decomp) and $[\alpha]_D^{26}$ of −198 (CHCl$_3$).

EXAMPLE 48

In 10 ml of anhydrous 1,2-dimethoxy ethane, 100 mg of the methylether derivative of TPC-A was dissolved and 240 mg of potassium fluoride-alumina and excess amount of methyl iodide were added and the mixture was shielded from the light while stirring at room temperature overnight. After completion of the reaction, the solution was filtered, the filtrate was subjected to distillation in vacuo to remove solvent and the residue obtained was purified by P-TLC followed by the recrystallization from methanol to obtain N-methyl derivative of the methylether of TPC-A (98 mg) as colorless crystal having m.p. of 285° to 292° C. (decomp) and $[\alpha]_D^{27}$ of −166° (CHCl$_3$).

EXAMPLE 49

In 5 ml of anhydrous DMF, 225 mg of TPC-A was dissolved and 11 mg of sodium hydride was added under ice cooling with stirring. According to a conventional method, 187 mg of bromide of acetyl D-glucose derived from acetyl D-glucose was added to the solution and then stirring was continued for 20 hours at room temperature. After the termination of the reaction, 50 ml of ethyl acetate was added and the solution was washed twice with ice water (20 ml each), and twice with saturated sodium chloride aqueous solution (20 ml each), then dried over anhydrous magnesium sulfate and subjected to distillation in vacuo to remove solvent and thus about 300 mg of product was obtained as white or light yellow hard oily material. To the oily material obtained, 10 ml of 5% potassium carbonate aqueous solution and 10 ml of methanol were added, the mixture was refluxed under heating for 1 hour with agitation, thereafter 30 ml of ice water was added and extracted thrice with 30 ml of ethylacetate. The combined extract was washed with 50 ml of saturated sodium chloride aqueous solution, then dried over anhydrous magnesium sulfate and subjected to distillation of solvent in vacuo to form about 200 mg of white solid material. The product was subjected to silicagel column chromatography and eluted with chloroform-methanol (10:0.5) mixed solvent to remove the soluble part, then eluted with the same mixed solvent (10:2) and the fractions eluted was collected. Thus, 53 mg of glucoside compound of TPC-A having m.p. of 210° to 216° C. (decomp) and $[\alpha]_D^{25}$ of −203° (EtOH).

Animal Test:

In this animal test, the antineoplastic action against the implanted tumor was examined in lower animals, in vivo, in respect of the compounds according to the present invention, by using CDF1 mice.

To the peritoneal cavity of each group of mice consisting of six CDF1 mice per group, $10^6$/0.1 ml of P-388 cells or $10^5$/0.1 ml of L-1210 cells were implanted. During 24 hours to 5 days after the implantation of the cells, the desired amount of the compounds of the present invention were administered intraperitoneally in an amount of 0.05, 0.5, 2, 4 or 10 mg/kg. While to the control groups of CDF1 mice, P-388 and L-1210 cells were implanted in the same manner and they were bred without administration of the compounds. The difference in the rate of apothanasia between them was observed and the results thereof are shown in Table 6.

TABLE 6

| P388 Compound | T/C % (Treatment/Control %) dose (mg/kg) | | | | |
|---|---|---|---|---|---|
| | 0.05 | 0.5 | 2 | 4 | 10 |
| Control | 100 | 100 | 100 | 100 | 100 |
| TPC-A | | | | | 187.4 |
| Methylether of TPC-A | 130.1 (dose, 0.01) | 156.7 | 164.2 | 173.6 | |
| Ex. 2 | 110.3 | 137.3 | 153.5 | 173.0 | |
| Ex. 3 | 137.3 | 165.4 | 162.2 | | |
| Ex. 5 | 142.4 | 175.1 | 105.4 | | |
| Ex. 7 | 122.2 | 142.7 | 165.4 | | |
| Ex. 8 | 115.8 | 144.7 | 150.1 | 164.0 | |
| Ex. 9 | 136.1 | 146.8 | 162.9 | 152.2 | |
| Ex. 10 | 112.5 | 141.5 | 150.1 | 155.4 | |
| Ex. 16 | 126.5 | 162.2 | 164.3 | | |
| Ex. 19(2) | 113.8 | 139.6 | 141.7 | 153.1 | |
| Ex. 20 | 138.4 | 164.3 | 121.1 | | |
| Ex. 21 | 133.6 | 143.2 | 151.6 | | 197.2 |
| Ex. 22 | 133.3 | 155.6 | 168.9 | | 194.7 |
| Ex. 23 | 129.0 | 145.3 | 164.4 | | 175.0 |
| Ex. 24 | 125.1 | 144.2 | 155.9 | | 170.0 |
| Ex. 25 | 124.1 | 150.7 | 155.9 | | 183.5 |
| Ex. 26 | 124.1 | 148.5 | 162.3 | | 186.6 |
| Ex. 27 | 117.9 | 149.5 | 157.9 | | 171.6 |
| Ex. 28 | 113.6 | 144.0 | 150.1 | | |
| Ex. 29 | 126.7 | 146.7 | 166.7 | | 168.9 |
| Ex. 30 | 122.0 | 146.3 | 151.6 | | 150.6 |
| Ex. 32 | 127.8 | 185.6 | 175.6 | | 183.3 |
| Ex. 40 | 111.6 | 133.9 | 152.1 | | |
| Ex. 41 | 117.9 | 147.4 | 158.9 | | |
| Ex. 42 | 114.6 | 140.0 | 159.2 | | |
| Ex. 43 | 116.6 | 142.0 | 154.2 | | |
| Ex. 44 | 116.6 | 150.1 | 165.3 | | |
| Ex. 45 | 121.7 | 145.0 | 162.3 | | |

In the Table, the symbol T/C % means Treatment/Control %, that is the increase in life when the control is 100. The values are obtained by implanting tumor cells to groups of mice (or rats), administering the compound being tested in various amounts every 24 hours after the implantation of the tumor cells and then calculating the ratio, the median survival time of the group to which the compound has been administered to the survival of the control, multiplied by a factor of 100. This method is used in the screening of U.S. National Cancer Institute.

As the screening test for confirming antineoplasticity of certain compound, it is known in the art that there are two kinds of tests, one being "in vitro" test wherein carcinoma cells in propagation in a test tube are used, the other being "in vivo" test wherein lower animals implanted with carcinoma cells are used. In Japan, the "in vivo" test is usually carried out by using Ehrlich tumor, L-1210 cells, sarcoma 180 cells, Yoshida sarcoma or ascites-liver tumor as ascitic tumor and immobilized carcinoma mentioned above as fixed carcinoma. Recently, a new method for confirming the antineoplasticity has been developed, in which lymphocytic leukemia cells P-388 are used. It is known that P-388 has more strong sensitivity than L-1210. As fixed carcinoma, there may be mentioned, for example Lewis lung cancer, B-16 melanoma, MM2, MOPC 104E, Colon 26, MH 134, C-1498 and the like.

The new compounds of the present invention were confirmed to be effective to the P-388 cells in the light of the screening test's results hereinbefore described. In addition, it is found that the ether derivatives and ester derivatives of TPC-A were effective against ascitic tumor other than P-388, in particular acetylester, capric acid ester and n-hexylether derivatives of TPC-A were found to be also effective against B-16 melanoma, MM2 (see Table 7).

In Table 7, the symbol "i.P.-i.P." means that the tumor cells are implanted intraperitoneally and the compounds being tested are also administered intraperitoneally. The symbol "TR" is the therapeutic ratio obtained by dividing the dose which provides a maximum T/C value, by the dose which provides a minimum T/C value.

The term in Table 7, last column "3/6 60<", means that 3 mice out of 6 mice continue to live more than 60 days after the implantation of the tumor cells.

TABLE 7

| Compound | Dose mg/kg | P388 (i.P. - i.P.) T/C (%) | L1210 (i.P. - i.P.) T/C (%) | B16 (i.P. - i.P.) T/C (%) | MM2 (i.P. - i.P.) T/C (%) |
|---|---|---|---|---|---|
| Methylether of TPC-A | 0.01 | 130.1 | 105.6 | — | — |
| | 0.5 | 156.7 | 118.6 | 133.8(0.25 mg/kg) | 103.1(0.2 mg/kg) |
| | 1 | 159.9(TR = 400) | 120.7 | 135.3 | 103.1 |
| | 2 | 164.2 | 129.3 | 139.1 | 118.4 |
| | 4 | 173.6 | 137.3(5 mg/kg) | 143.0 | 90.8(5 mg/kg) |
| Ex. 22 | 0.05 | 133.3 | 100.9 | — | — |
| | 0.5 | 155.6 | 110.0 | 116.9 | 102.5 |
| | 2 | 168.9(TR = 278) | 114.4 | 128.5 | 109.2 |
| | 5 | 175.8 | 120.0 | 147.8(4 mg/kg) | 117.8 |
| | 10 | 194.7 | 128.9 | 141.1(8 mg/kg) | 120.9 |
| Ex. 2 | 0.05 | 130.4 | — | — | — |
| | 0.5 | 143.5 | 115.6 | 130.5 | 110.3 |
| | 2 | 150.0(TR ≈ 100) | 126.6 | 158.2 | 129.3(3/6 60<) |
| | 4 | — | 130.9 | 136.2 | 161.8(1/7 60<) |
| | 5 | 176.1 | — | — | — |
| Ex. 21 | 0.01 | 133.7 | — | — | — |
| | 0.1 | 135.9 | — | — | — |
| | 0.5 | — (TR ≈ 200) | 115.6 | 143.5 | 112.1 |
| | 2 | 152.2 | 126.6 | 152.0 | 127.3(2/6 60<) |
| | 5 | — | 67.3(10 mg/kg) | 165.5 | 93.9(10 mg/kg) |

Toxicity Test:

With respect to the compounds of this invention, the lethal dose was determined as follows.

By using male 4-weeks CD-1 (ICR) mice consisting of 5 to 10 mice per group, the desired amount of each compound of this invention was suspended in 0.5% CMC solution and the resultant suspension was administered to each mouse intraperitoneally or intravenously. Observing the life or death as well as the general symptom during 7 days after the administration of the compounds, the value of $LD_{50}$ for each compounds was estimated from the lethal population observed on the basis of the Litchfield-Wilcoxon method. The results are shown in Table 8.

TABLE 8

| Manner of administration | LD$_{50}$ and 95% Confidence Limit (mg/kg) | | |
|---|---|---|---|
| | TPC-A | Methylether of TPC-A | acetylester TPC-A |
| intraperitoneal | 126.0(13.3–19.3) | 10.0(7.0–14.3) | 18.4(16.9–20.0) |
| intravenous | 34.0(28.1–41.2) | 16.5(12.6–21.5) | 20.0(15.2–26.3) |

As will be seen from the result shown in Table 8, the values of LD$_{50}$ of the compounds listed above are lower in the intraperitoneal administration than in the intravenous administration. The tendency is quite different from that of usual medicines.

Additional tests are reported in Table 9 hereinbelow:

| Compound | Dose × period of administration (days) | |
|---|---|---|
| "P 388" (ip-iv) | | T/C |
| TPC-A | 5.56 mg/kg × 9 | 121.4% |
| Methylether of TPC-A | 0.56 mg/kg × 9 | 115.7% |
| | 2.22 mg/kg × 9 | 160.8% |
| Ex. 2 | 5 mg/kg × 5 | 118.9% |
| Ex 22 | 1.11 mg/kg × 9 | 112.5% |
| | 5.56 mg/kg × 9 | 171.5% |
| Ex 21 | 5.56 mg/kg × 9 | 117.2% |
| | 6.94 mg/kg × 9 | 120.4% |
| (sc-iv) | | |
| TPC-A | 5 mg/kg × 7 | 179.6(2/7 60<) |
| | 7 mg/kg × 7 | 153.7(1/7 60<) |
| | 10 mg/kg × 7 | 127.8 |
| "Colon 26" (ip-ip) | | |
| Ex 2 | 4 mg/kg × 9 | 133.7%(2/6 60<) |
| Methylether of TPC-A | 1 mg/kg × 9 | 113.6% |
| | 2 mg/kg × 9 | 125.0% |
| | 4 mg/kg × 9 | 125.9% |
| "MM2" (ip-ip) | | |
| TPC-A | 2.78 mg/kg × 9 | 138.7% |
| | 5.56 mg/kg × 9 | 231.2%(2/6 60<) |
| | 6.94 mg/kg × 9 | 184.3%(1/7 60<) |
| "Yoshida sarcoma" (ip-ip) | | |
| Ex 21 | 0.1 mg/kg × 5 | 167.0% |
| | 0.5 mg/kg × 5 | 200.0% |
| | 1 mg/kg × 5 | 213.3%(2/6 30<) |
| | 2.5 mg/kg × 5 | 167.0% |
| Ex 2 | 0.1 mg/kg × 5 | 129.7% |
| | 0.5 mg/kg × 5 | 173.6% |
| | 1.0 mg/kg × 5 | 160.4% |
| | 2.5 mg/kg × 5 | 149.5% |
| (ip-iv) | | |
| Ex 21 | 0.83 mg/kg × 9 | 116.7% |
| | 1.11 mg/kg × 9 | 124.8% |
| "P 388" (ip-ip) | (in combination with a known medicin) | |
| Mitomycin | 0.5 mg/kg × 5 | 198.2% |
| Mitomycin | 0.5 mg/kg ⎫ × 5 | 246.8% |
| Ex 21 | 0.5 mg/kg ⎭ | |
| Mitomycin | 0.5 mg/kg ⎫ × 5 | 270.3% |
| Ex 21 | 5 mg/kg ⎭ | |
| "Erlich carcinoma" (sc-ip) | | Inhibition |
| Ex 21 | 8 mg/kg × 11 | (after 14 days) 58.5% |
| Ex 22 | 4 mg/kg × 11 | (after 14 days) 46.9% |
| Methylether of TPC-A | 2 mg/kg × 11 | (after 14 days) 60.5% |
| "Lewis Lung Carcinoma" (sc-ip) | | |
| Ex 21 | 0.5 mg/kg × 25 | (after 17 days) 24.3% |
| Ex 22 | 8 mg/kg × 11 | (after 17 days) 65.4% |
| Methylether of TPC-A | 4 mg/kg × 11 | (after 17 days) 51.1% |
| "Colon. 38" (sc-ip) | | |
| Ex 22 | 8 mg/kg × 11 | (after 17 days) 51.9% |
| Methylether of TPC-A | 4 mg/kg × 11 | (after 17 days) 70.1% |
| "MOPC-104E" (ip-ip) | | T/C |
| Ex 21 | 2 mg/kg × 9 times | 120.5% |
| | 5 mg/kg × 9 times | 136.8% |
| Ex 2 | 2 mg/kg × 9 times | 145.3% |
| "C-1498" (ip-ip) | | |
| Ex 21 | 2 mg/kg × 5 days | 110.2% |
| | 8 mg/kg × 5 days | 122.2% |
| "L1210" (ip-ip) | | |
| Ex 32 | 2 mg/kg × 5 days | 132.3% |
| | 8 mg/kg × 5 days | 127.7% |
| Ex 48 | | |
| "P 388" (ip-ip) | 0.5 mg/kg × 5 | 124.8 |
| | 4 mg/kg × 5 | 148.3 |
| | 8 mg/kg × 5 | 161.0 |
| | 10 mg/kg × 5 | 170.0 |
| "P 388" (ip-iv) | 3.33 mg/kg × 5 | 132.2 |
| | 5 mg/kg × 5 | 145.6 |
| | 6.67 mg/kg × 5 | 141.8 |
| "MM2" (ip-ip) | 2.78 mg/kg × 9 | 154.6 |
| | 5.56 mg/kg × 9 | 166.6 |
| "MM2" (ip-iv) | 5.56 mg/kg × 9 | 131.6 |
| "B16" (ip-ip) | 0.56 mg/kg × 9 | 123.4 |

In Table 9, "iv" and "sc" means that the administration of the compounds is carried out intravenously and the implantation of the tumor cells is carried out subcutaneously.

In this test, other pharmacological effects which may be obtained by these compounds were investigated.

Each compound of the invention was intraperitoneally administered to 4-weeks CD-1 (IRC) mice (Nippon Charles Liver K.K.) in the dose of 1 to 20 mg/kg with using mice groups consisting of three mice per group. The symptom of the mice was observed at every 30 minutes after the administration of the compound for 180 minutes. The observation was carried out according to the modified Arwin method and Smith method, i.e., neuropharmacological multidimentional observation method.

Making a comparison between the symptom observed and the pattern of the pharmacological action due to the known medicines, it has been discovered that each compound of the invention has the following pharmacological effect.

TABLE 9

| Compound | Pharmacological effect estinated |
|---|---|
| TPC-A | emetic action, anorexigenic action, psychotropic action, vasoconstrictive action, papaverine action, antiperkinsonian action. |
| Methylether of TPC-A | emetic action, anorexigenic action. |
| Acetic acid ester of TPC-A | emetic action, psychotropic action, antidiuretic action. |

What is claimed is:

1. The method of inducing remission of a malignancy in a subject affected by said malignancy, which consists of administering an effective dose of a compound of formula [I]:

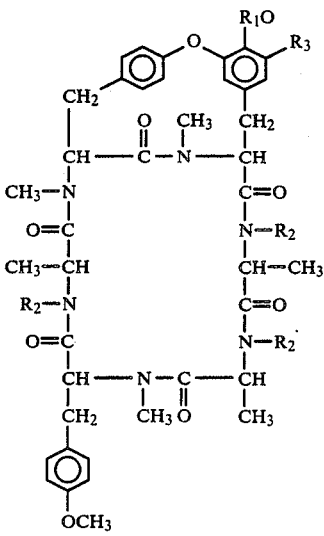

wherein $R_1$ is
(a) an acyl group of formula —COA, A being a linear or branched saturated or unsaturated $C_1$-$C_{17}$ alkyl, phenyl or a phenyl substituted by a halogen atom, lower alkyl, nitro or amino group; benzyl or styryl group unsubstituted or substituted by a halogen atom, lower alkyl, nitro or amino group;
(b) a linear or branched $C_1$-$C_{18}$ alkyl;
(c) $C_5$-$C_6$ cycloalkyl;
(d) $C_2$-$C_4$ carboxyalkyl or an ester thereof with a $C_1$-$C_2$ alcohol;
(e) tetrahydropyran;
(f) glucose;
(g) —$SO_2CH_3$ or hydrogen;
$R_2$ is hydrogen or methyl and
$R_3$ is hydrogen, amino or nitro
(e) tetrahydropyran;
(f) glucose;
(g) —$SO_2CH_3$ or hydrogen;
$R_2$ is hydrogen or lower alkyl and
$R_3$ is hydrogen, amino or nitro.

2. The method according to claim 1, wherein said effective dose is 0.05–10 mg/kg of body weight of said subject.

3. The method according to claim 1, wherein said malignancy is (a) P-388 leukemia cells, (b) MM2 mammary carcinoma cells, (c) Colon 26 cells, (d) Yoshida Sarcoma cells, (e) Erlich carcinoma cells, (f) Lewis Lung Carcinoma cells, (g) Colon Adenocarcinoma cells, (h) MOPC-104E cells, (i) C-1498 leukemia cells, (j) L1210 leukemia cells, (k) B-16 melanoma cells and (l) Colon Adenocarcinoma 38 cells.

4. The method of increasing the activity of Mitomycin in the treatment of a subject affected by P-338 cells, which consists of administering to said subject Mitomycin in the amount of 0.5 mg/kg of body weight of said subject together with a compound according to claim 1, in the amount of 0.5–5 mg/kg of body weight of said subject.

* * * * *